United States Patent [19]

Dodd et al.

[11] Patent Number: 5,674,478
[45] Date of Patent: Oct. 7, 1997

[54] HAIR CONDITIONING COMPOSITIONS

[75] Inventors: Michael Thomas Dodd, Edgewood, Ky.; John Paul Featherston; David Junior Raney, both of Cincinnati, Ohio

[73] Assignee: The Procter & Gamble Company, Cincinnati, Ohio

[21] Appl. No.: 586,397

[22] Filed: Jan. 16, 1996

[51] Int. Cl.$^6$ ............................................. A61K 7/075
[52] U.S. Cl. ............... 424/70.1; 424/70.11; 424/70.12; 424/70.15; 424/70.16; 424/70.17
[58] Field of Search .................... 424/70.11, 70.16, 424/70.17, 70.12, 70.15

[56] References Cited

U.S. PATENT DOCUMENTS

| | | | |
|---|---|---|---|
| 4,488,564 | 12/1984 | Grollier | 132/7 |
| 4,493,824 | 1/1985 | Abe | 424/70 |
| 4,705,681 | 11/1987 | Maes et al. | 424/70 |
| 4,900,545 | 2/1990 | Wisotzki et al. | 424/70 |
| 4,913,743 | 4/1990 | Brode et al. | 106/162 |
| 4,943,430 | 7/1990 | Hefford et al. | 424/70.11 |
| 5,100,660 | 3/1992 | Hawe et al. | 424/78.35 |
| 5,104,646 | 4/1992 | Bolich, Jr. et al. | 424/70.11 |
| 5,136,093 | 8/1992 | Smith | 564/197 |
| 5,139,772 | 8/1992 | Morita et al. | 424/70 |
| 5,173,290 | 12/1992 | Halloran | 424/70.1 |
| 5,211,941 | 5/1993 | Komori et al. | 424/70 |
| 5,306,489 | 4/1994 | Goldberg | 424/47 |
| 5,332,569 | 7/1994 | Wood et al. | 424/70 |
| 5,342,611 | 8/1994 | Komori et al. | 424/70 |
| 5,362,484 | 11/1994 | Wood et al. | 424/70 |
| 5,368,850 | 11/1994 | Cauwet et al. | 424/73 |
| 5,417,965 | 5/1995 | Janchitraponvej | 424/70.12 |
| 5,470,884 | 11/1995 | Corless et al. | 514/864 |
| 5,540,853 | 7/1996 | Trinh et al. | 510/101 |

FOREIGN PATENT DOCUMENTS

| | | | |
|---|---|---|---|
| 9462606 | 9/1994 | Australia | A61K 7/48 |
| 0 473 349 B1 | 3/1992 | European Pat. Off. | A61K 7/06 |
| 0 515 270 A2 | 11/1992 | European Pat. Off. | A61K 7/48 |
| 0 535 367 A2 | 4/1993 | European Pat. Off. | A61K 7/06 |
| 57-149213 | 9/1982 | Japan | A61K 7/00 |
| 61-26001 | 11/1986 | Japan | A61K 7/08 |
| 04230614 | 8/1992 | Japan | A61K 7/06 |
| 8608856 | 12/1986 | Spain | A61K 7/08 |
| 94/14404 | 7/1994 | WIPO | A61K 7/075 |

OTHER PUBLICATIONS

Weiser et al. "Acceleration of Superficial Wound Healing by Panthenol Zinc Oxide," Cosmetics Toiletries, vol. 103, pp. 79–84, Oct., 1988.

*Primary Examiner*—Amy Hulina
*Attorney, Agent, or Firm*—Anthony D. Sabatelli

[57] ABSTRACT

The present invention relates to a leave-on hair care composition comprising: (i) from about 0.1% to about 10%, by weight, of a cationic crosslinked polymeric conditioning agent comprising the monomer units $(A)_m$ $(B)_n$ $(C)_p$ and a crosslinking agent wherein: (A) is a dialkylaminoalkyl acrylate monomer or a quaternary ammonium or acid addition salt thereof; (B) is a dialkylaminoalkyl methacrylate monomer or a quaternary ammonium or acid addition salt thereof; (C) is a nonionic monomer polymerizable with (A) or (B); m, n, and p are independently zero or greater, but at least one of m or n is one or greater; (ii) from about 0.1% to about 10%, by weight, of a salt; and (iii) from about 60% to about 99.8%, by weight, of a polar solvent; wherein the weight ratio of said cationic crosslinked polymeric conditioning agent to said salt is from about 1:25 to about 25:1; wherein the viscosity of the composition is from about 10 cP to about 500 cP as measured using a Brookfield Viscometer, Spindel #41, at 25° C., at 10 RPM for three minutes.

4 Claims, No Drawings

HAIR CONDITIONING COMPOSITIONS

TECHNICAL FIELD

The present invention relates to leave-on hair care compositions which provide improved hair conditioning properties. These compositions comprise a cationic crosslinked polymeric conditioning agent, a salt and a polar solvent. These products have an unexpected low viscosity compared to traditional products containing said conditioning agents. The low viscosity of the compositions allows for the use of said compositions as leave-on products such as hair tonics, hair sprays, mousses and the like.

BACKGROUND OF THE INVENTION

Scalp hair becomes soiled due to its contact with the surrounding environment and from sebum secreted from the hair follicles. The build-up of sebum and environmental soiling can cause the hair to have a dirty or greasy feel, and an unattractive appearance. In order to ameliorate these effects, it is necessary to shampoo the hair with regularity.

Shampooing the hair removes excess sebum and other environmental soiling but has the disadvantage of leaving the hair in a wet, tangled, and relatively unmanageable state. Shampooing can also result in the hair becoming dry due to the removal of natural oils or other hair moisturizing materials. After shampooing, the hair can also suffer from a perceived loss of "softness." Frequent shampooing also contributes to the phenomena of "split ends," particularly for long hair. Split ends refers to a condition wherein the ends of the hair are split into two or more shafts, resulting in a frizzy appearance.

A variety of approaches have been developed to condition the hair. These range from post-shampooing hair rinses, to leave-on hair conditioner tonics and sprays, to the inclusion of hair conditioning components in shampoos. Although many consumers prefer the ease and convenience of a shampoo which includes conditioners, a substantial proportion prefer using the conditioner formulations which are applied to the hair as a separate step from shampooing, usually subsequent to shampooing. These hair conditioners are typically either a thickened product, such as a cream rinse or gel for ease of dispensing and application to the hair in the bath or shower, or a low viscosity product, such as a tonic, spray or mousse for ease of dispensing and application to the hair after the bath or shower.

Low viscosity hair care conditioning compositions such as hair tonics, hair conditioning sprays and mousses are also well know in the art. These products are useful in their ability to deliver hair care styling or conditioning agents to the hair with minimal wax or surfactant residue from the composition itself.

Crosslinked polymeric conditioning agents have been disclosed in the art as conditioning agents, thickening agents or hair damage prevention agents. PCT patent application no. WO 94/10833, to Cox et al., published Apr. 13, 1995 discloses hair care compositions containing crosslinked polymeric conditioning agents in compositions for improved hair shine benefits. These conditioning agents, although effective, have a viscosity building effect and are most suitable for cream and lotion shampoos and conditioners. However, the resulting high viscosities of hair care compositions containing these crosslinked polymeric conditioning agents have prevented the use of these agents in low viscosity products such as hair tonics, hair sprays, mousses and the like.

It has been unexpectedly found in the present invention that hair care compositions containing crosslinked polymeric conditioning agents can be provided in the form of low viscosity products, when used in conjunction with salt. These hair care compositions provide the conditioning and damage prevention benefits of the cationic crosslinked polymeric conditioning agents in low viscosity products.

It is an object of this invention to provide hair care compositions for application to the hair which are not rinsed off after use.

It is another objective of the present invention to provide said compositions in a low viscosity form.

It is a further object of the present invention to provide said compositions as a hair tonic, hair spray or mousse, which can be easily applied, either before of after drying of the hair.

It is a further object of this invention to provide such a hair care composition that has an aesthetically pleasing wet and dry hair feel.

It is another objective of the present invention to provide a method for conditioning hair with the above compositions.

These and other objects and benefits of the present invention as may be set forth herein as may now or later become apparent to those skilled in the art can be provided according to the invention which is described herein.

The invention hereof can comprise, consist of, or consist essentially of the essential elements described herein as well as any of the preferred or other optional ingredients described herein.

All percentages herein are by weight of the total composition unless otherwise indicated. All ratios are weight ratios unless otherwise indicated. Unless otherwise indicated, all percentages, ratios, and levels of ingredients referred to herein are based on the actual amount of the ingredient, and do not include solvents, fillers, or other materials with which the ingredient may be combined in commercially available products. All measurements are at 25° C. or room temperature, unless otherwise designated.

All documents referred to herein, including all patents, all patent applications, all articles, all bulletins, all pamphlets, and all technical data sheets are incorporated herein by reference in their entirety.

SUMMARY OF THE INVENTION

The present invention relates to leave-on hair care compositions that can provide enhanced hair conditioning and damage prevention, while being formulated in a low viscosity product for ease of application after bathing or showering. In particular, the present invention relates to leave-on hair care compositions comprising:

(i) from about 0.1% to about 10%, by weight, of a cationic crosslinked polymeric conditioning agent comprising the monomer units $(A)_m$ $(B)_n$ $(C)_p$ and a crosslinking agent wherein:
  (A) is a dialkylaminoalkyl acrylate monomer or a quaternary ammonium or acid addition salt thereof;
  (B) is a dialkylaminoalkyl methacrylate monomer or a quaternary ammonium or acid addition salt thereof;
  (C) is a nonionic monomer polymerizable with (A) or (B);
  m, n, and p are independently zero or greater, but at least one of m or n is one or greater;

(ii) from about 0.1% to about 10%, by weight, of a salt; and (iii) from about 60% to about 99.8%, by weight, of a polar solvent;

wherein the weight ratio of said cationic crosslinked polymeric conditioning agent to said salt is from about 1:25 to about 25:1;

wherein the viscosity of the composition is from about 10 cP to about 500 cP as measured using a Brookfield Viscometer, Spindel #-41, at 25° C., at 10 RPM for three minutes.

The present invention also relates to methods for conditioning human hair comprising the application of a safe and effective amount of the hair care composition described above to the hair of a human in need of such treatment.

DETAILED DESCRIPTION OF THE INVENTION

The term "leave-on", as expressed herein to modify the term "hair care composition", is used to indicate that the compositions of the present invention are intended to be applied to and allowed to remain on the hair. These leave-on compositions are to be distinguished from "rinse-off" compositions which are applied to the hair and subsequently removed, either immediately or after a few minutes, either by washing, rinsing, wiping or the like.

The essential ingredients as well as a variety, but non-exclusive, list of preferred and optional ingredients are described below.

Cationic Crosslinked Polymeric Conditioning Agent

The compositions of the present invention comprise from about 0.1% to about 10%, more preferably from about 0.2% to about 5%, and most preferably from about 0.5% to about 3% of a cationic crosslinked polymer conditioning agent. The cationic crosslinked polymers hereof provide improved hair conditioning and damage prevention benefits upon application to the hair.

Crosslinked polymers of the type for use herein are generally described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The polymers hereof can be characterized by the general formula: $(A)_m(B)_n(C)_p$ wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a nonionic monomer that is polymerizable with (A) or (B) having a carbon-carbon double bond, that is polymerizable with (A) or (B), m is an integer of 0 or greater, n is an integer of 0 or greater, and p is an integer of 0 or greater, wherein either m or n, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, most preferably $C_1$–$C_2$. When quaternized, the polymers are preferably quaternized with short chain alkyls, i.e., $C_1$–$C_8$, preferably $C_1$–$C_5$, more preferably $C_1$–$C_3$, most preferably $C_1$–$C_2$. The acid addition salts refer to the (A) and (B) monomers of the polymers having protonated amino groups. Acid addition salts can be pre-formed through the use of halogen (e.g. chloride), acetic, phosphoric, nitric, citric, or other acids.

These $(A)_m(B)_n(C)_p$ polymers also contain a crosslinking agent, which is typically a material containing two or more unsaturated functional groups. The crosslinking agent is reacted with the monomer units of the polymer and is incorporated into the polymer, forming either links or covalent bonds between two or more individual polymer chains or between two or more sections of the same polymer chain. Nonlimiting examples of suitable crosslinking agents include those selected from the group consisting of methylenebisacrylamides, diacrylates, dimethacrylates, di-vinyl aryl (e.g. di-vinyl phenyl ring) compounds, poly-alkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol, propylene glycol, butylene glycol, di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, 1,4 di-ethylene benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. The crosslinking agent will typically comprise from about 1 ppm to about 10,000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer can be measures to characterize the polymer. This intrinsic viscosity is distinct from the viscosity measurement used to characterize the total hair care composition of the present invention. The intrinsic viscosity of the crosslinked polymer can measured in one molar sodium chloride solution at 25° C., is generally above 6, preferably from about 8 to 14. The molecular weight (weight average) of the crosslinked polymers hereof is high, and is believed to typically be between about 1 million and about 30 million. The specific molecular weight is not critical and lower or higher weight average molecular weights can be used. The crosslinked polymers are preferably characterized in a 1.0% solution of the polymer in deionized water to have a viscosity, at 25° C., of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of C, based on the total molar amount of A, B, and C, can be from 0% to about 99%. The molar proportions of (A) and (B) can each be from 0% to 100%. When acrylamide is used as the "C" monomer, it will preferably be used at a level of from about 20% to about 99%, more preferably from about 50% to about 90%.

Where monomer A and B are both present, the ratio of monomer A:monomer B in the final polymer, on a molar basis, is preferably about 99:5 to about 15:85, more preferably from about 80:20 to about 20:80.

Alternatively, in another class of polymers, the ratio is from about 5:95 to about 50:50, preferably from about 5:95 to about 25:75.

In another alternative class the ratio A:B is from about 50:50 to about 85:15. Preferably the ratio A:B is from about 60:40 to about 85:15, most preferably from about 75:25 to about 85:15.

Most preferred in the present invention is where neither monomer A nor monomer C is present Cationic polymers useful herein that are especially preferred are those conforming to the general structure $(A)_m(B)_n(C)_p$ wherein m is zero, (B) is methyl quaternized dimethylaminoethyl methacrylate, p is zero, and the crosslinking agent is methylenebisacrylamide. An example of such a homopolymer is polyquaternium 37. The homopolymer can be used alone or in a suitable carrier such as mineral oil or propylene glycol dicaprylate/dicaprate. This homopolymer is commercially available as a mineral oil dispersion also containing PPG-1 trideceth-6 as a dispersing aid, from Allied Colloids Ltd., (Norfolk, Va.) under the trademark Salcare® $SC_{95}$ or as a dispersion in propylene glycol dicaprylate/dicaprate also containing PPG-1 trideceth-6 as a dispersing aid, from Allied Colloids Ltd, (Norfolk, Va.) under the trademark Salcare® $SC_{96}$.

Salt

The compositions of the present invention comprise from about 0.1% to about 10%, more preferably from about 0.2% to about 5%, and most preferably from about 0.5% to about 3% of a salt. Without being limited by theory, the salt is believed to provide a viscosity reduction effect on the polymer in the polar solvent of the present invention.

The salt of the present invention comprises a mixture of monomeric cations and anions. The salt Of the present invention comprises monomeric ions of the type which are products of acid-base reactions. The salt can be incorporated into the hair care compositions, for example, by addition of soluble salts, or by addition of mixtures of acids and bases, or by a combination thereof. It is a necessary aspect of the invention that both anions and cations of the salt be included in the composition.

Suitable cations for use include, for example, alkali metals, such as lithium, sodium, and potassium, alkaline-earth metals, such as magnesium, calcium, and strontium, and transition metals such as aluminum, copper, zinc, iron and the like. Preferred of the divalent cations is magnesium. Preferred monovalent metal ions are lithium, sodium, and potassium, particularly sodium and potassium. Suitable means of addition to the compositions hereof include, for example, addition as bases, e.g., hydroxides, sodium hydroxide and potassium hydroxide, and such as salts that are soluble in the polar solvent, e.g. salts of monomeric anions such as those described below.

Other suitable cations include organic ions, such as quaternary ammonium ions and cationic amines, such as ammonium mono-, di-, and tri-ethanolamines, triethylamine, morpholine, aminomethylpropanol (AMP), aminoethylpropanediol, etc. Ammonium and the amines are preferably provided in the forms of salts, such as hydrochloride salts.

Anions that can be used include halogen ions, such as chloride, fluoride, bromide, and iodide, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, acetate, ethylene diamine tetra acetate and other anions that can exist in dissociated form in the hair care composition. The anions can be added to the compositions hereof, for example, in the form of acids or salts which are at least partially soluble in the liquid vehicle. Preferred anions include acetate, ethylene diamine tetra acetate, citrate, nitrate, chloride, phosphate and sulfate, etc. More preferred is ethylene diamine tetra acetate.

The salts of the compositions of the present invention must be soluble in the polar solvent to achieve the desired viscosity reduction benefit. The solubility of the salts is greater than about 1 percent, preferably greater than about 2 percent and more preferably greater than about 3%. All solubility measurements are taken at 25° C.

Preferred salts of the compositions of the present invention include sodium acetate, potassium acetate, ammonium acetate, sodium citrate, potassium citrate, ammonium citrate, sodium nitrate, potassium nitrate, ammonium nitrate, sodium phosphate, potassium phosphate, ammonium phosphate, sodium chloride, potassium chloride, ammonium chloride, sodium sulfate, potassium sulfate, ammonium sulfate, sodium ethylene diamine tetra acetic acid, disodium ethylene diamine tetra acetic acid and trisodium ethylene diamine tetra acetic acid, tetra sodium ethylene diamine tetra acetate and mixtures thereof. Most preferred is disodium ethylene diamine tetra acetic acid.

Ratio of Crosslinked Polymeric Conditioning Agent to Salt

The compositions of the present invention must comprise a critical weight ratio of cationic crosslinked polymeric conditioning agent to salt of from about 1:25 to about 25:1, preferably from about 1:10 to about 15:1, and more preferably from about 1:1 to about 10:1.

Polar Solvent

The leave-on hair care compositions of the present invention also comprise a polar solvent as a liquid vehicle for the crosslinked polymeric conditioning agent. A polar solvent is any solvent material with a dielectric constant at 25° C. greater than about 5.0, preferably greater than about 7.5 and more preferably greater than about 10.0. The polar solvent of the present invention comprises one or more polar solvents that are present in the hair care compositions at a level of from about 60% to about 99.8%, preferably from about 80% to about 98%, more preferably from about 90% to about 95% of the total composition.

The polar solvents essential to the present compositions are selected from the group consisting of water, $C_2$–$C_3$ monohydric alkanols, and mixtures thereof. If present, $C_3$ alkanols, such as isopropanol, should be used at levels no greater than about 15% by weight of the composition, preferably no greater than about 12%, more preferably no greater than about 10%. High levels of $C_3$ monohydric alcohols are undesirable in the present compositions due to potential odor issues they can create. Preferred polar solvent phases contain water, ethanol, or mixtures thereof.

Where water and alcohol mixtures are used, for instance, water-ethanol or water-isopropanol-ethanol, the water content of the compositions is generally in the range of from about 0.5% to about 99%, by weight of the total composition. In such mixtures, the alcohol solvents am generally present in the range of from 0.5% to about 99%, by weight of the total composition.

Viscosity

The composition of the present invention mixture comprising a viscosity, at 25° C., of from about 10 to about 500 cP, preferably from about 50 cP to about 200 cP, and more preferably from about 100 cP to about 200 cP. Viscosity is determined using a Brookfield Digital Viscometer Model DV-II, Spindel #41, at 25° C., at 10 RPM for three minutes.

Optional Ingredients

The hair care compositions of the present invention can be formulated in a variety of product types which have low viscosity, including tonics, sprays and mousses. Therefore the present compositions can contain a wide variety of optional ingredients, including among them any of the types of ingredients known in the art for use in hair care products, especially hair spray and hair tonic compositions. These ingredients include, but are not limited to, insoluble silicone fluids, gums and resins, volatile silicone solvents, non-solubilzed particulates, surfactants, dispersing aids, styling resins, propellants and others.

Silicone Conditioning Agents

The compositions hereof can optionally include nonvolatile soluble or insoluble silicone conditioning agents or volatile silicone conditioning agents. By soluble what is meant is that the silicone conditioning agent is miscible with the aqueous carrier of the composition so as to form part of the same phase. By insoluble what is meant is that the silicone forms a separate, discontinuous phase from the aqueous carrier, such as in the form of an emulsion or a suspension of droplets of the silicone. The term "nonvolatile" as used herein shall mean that the silicone has a boiling point of at least about 260° C., preferably at least about 275° C., more preferably at least about 300° C. Such materials exhibit very low or no significant vapor pressure at ambient conditions. The term volatile shall mean that the silicone has a boiling point of from about 99° C. to about 260° C.

The silicone hair conditioning agent will be used in the leave-on hair care compositions of the present invention at levels of from about 0.05% to about 10% by weight of the composition, preferably from about 0.1% to about 6%, more preferably from about 0.5% to about 5%, most preferably from about 0.5% to about 3%.

Soluble silicones include silicone copolyols, such as dimethicone copolyols, e.g. polyether siloxane-modified polymers, such as polypropylene oxide, polyethylene oxide modified polydimethylsiloxane, wherein the level of ethylene and/or propylene oxide sufficient to allow solubility in the composition.

Preferred, however, are insoluble silicones. The insoluble silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 300,000.

Silicone fluids hereof also include polyalkyl or polyaryl siloxanes with the following structure:

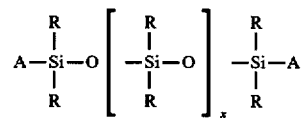

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their Viscasil R® and SF96® series, and from Dow Corning in their Dow Corning 200® series.

The polyalkylaryl siloxane fluids that may be used, also include, for example, polymethylphenylsiloxanes. These siloxanes are available, for example, from the General Electric Company as SF1075® methyl phenyl fluid or from Dow Corning as 556 Cosmetic Grade Fluid®.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The polyether siloxane copolymers that may be used include, for example, a polypropylene oxide modified polydimethylsiloxane (e.g., Dow Corning DC-1248®) although ethylene oxide or mixtures of ethylene oxide and propylene oxide may also be used. The ethylene oxide and polypropylene oxide level should be sufficiently low to prevent solubility in the composition hereof.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference.

Another silicone hair conditioning material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,0.00 centistokes, wherein the ratio of gum to fluid is from about 30:70 to about 70:30, preferably from about 40:60 to about 60:40. The gum fluid blend can be used alone or in a premix with a suitable carrier such as polysorbate 80.

An optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230® and SS4267®. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Another optional silicone conditioning agent is volatile silicone solvent. The volatile silicone solvent, if present, is at a level of from about 0.01% to about 10%, preferably from about 0.05% to about 5%, by weight, of the composition. The volatile silicone allows for easier and more even dispersion of silicone gums and resins in hair care compositions. The silicones may be either cyclic or linear polydimethyl siloxanes. The number of silicon atoms in the cyclic silicones is from about 3 to about 7, most preferably 4 or 5. The general formula for the cyclic silicones is:

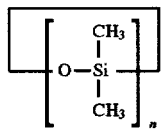

wherein n=3–7. Linear polydimethyl siloxanes useful in the present invention generally contain from about 3 to about 9 silicon atoms and have the general formula:

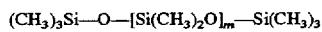

wherein m=1–7.

Volatile silicone solvents of the above described types are widely available, e.g. from Dow Corning as 344, 345 and 200 Fluids®; Union Carbide as Silicone 7202 and 7158®;and Stauffer Chemical as SWS-03314®. The preferred volatile silicone solvent of the present invention is cyclomethicone available from General Electric Silicones. If present, it is present at from about 0.05% to about 5.0%.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Hair Styling Resins

Another optional ingredient of the hair care compositions of the present invention is hair styling resins. Any hair hold polymer soluble or dispersible in the polar solvent phase of the present invention may be used. Suitable types of polymers include anionic, non-ionic, amphoteric and cationic polymer materials. Specific polymers include polyvinylpyrrolidone (PVP), copolymers of PVP and methylmethacrylate, copolymers of PVP and vinylacetate (VA), poylvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethymethacrylate/methacrylic acid terpolymer, vinyl acetate/crotonic acid/vinyl neodecanoate copolymer, octylacrylamide/acrylates copolymer, monoethy ester of poly(methyl vinyl ether-maleic acid), and octylacrylamide/acrylate/butylaminoethyl methacrylate copolymers, acrylic acid/t-butyl acrylate copolymers, dimethylaminoethyl methacrylate/isobutyl methacrylate/2-ethylhexyl-methacrylate terpolymers, t-butylacrylate/acrylic acid copolymers, and silicone grafted terpolymers, e.g. t-butylacrylate/acrylic acid/PDMS and mixtures thereof. PVP and PVP copolymers with other monomers are preferred. The most preferred resins for use in the present hair care compositions are copolymers of polyvinyl pyrrolidone and vinyl acetate (PVPNA).

Additional hair styling polymers which can be optionally added to the compositions of the present invention include silicone-containing hair styling resins. The silicone-containing polymers are characterized by polysiloxane moieties covalently bonded to and pendant from a polymeric carbon-based backbone. The backbone is preferably a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The preferred silicone-containing polymers comprise an organic backbone preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone.

Silicone-containing polymers disclosed in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No.

5,100,657, Ansher-Jackson, et al., issued Mar. 31, 1992, U.S. Pat. No. 5,104,646, Bolich et al., issued Apr. 14 1992 U.S. Ser. No. 07/758,319 Bolich et al, filed Aug. 27, 1991 now abandoned and U.S. Ser. No. 07/758,320 Torgerson et al., filed Aug. 27, 1991, now abandoned all of which are incorporated by reference herein.

When used, the hair styling resins are used at a level of from about 0.25% to about 20%, preferably from about 0.5% to about 10% of the composition.

Other Ingredients

The compositions of the present invention can comprise a wide range of additional components suitable for rendering such compositions more cosmetically or aesthetically acceptable or to provide them with additional usage benefits. The *CTFA Cosmetic Ingredient Handbook*, Second Edition, 1992, which is incorporated by reference herein in its entirelty, describes a wide variety of nonlimiting cosmetic ingredients commonly used in the hair care industry. These additional ingredients include: other conditioning agents; detersive surfactants, such as anionic, nonionic, amphoteric, and zwitterionic surfactants; suspending agents, such as xanthan gum, guar gum, hydroxyethyl cellulose, methyl cellulose, hydroxyethylcellulose, starch and starch derivatives; preservatives such as benzyl alcohol, methyl paraben, propyl paraben and imidazolidinyl urea; pH adjusting agents; coloring agents, such as any of the FD&C or D&C dyes; hair oxidizing (bleaching) agents, such as hydrogen peroxide, perborate and persulfate salts; hair reducing agents, such as the thioglycolates; perfumes; polymer plasticizing agents, such as glycerin, disobutyl adipate, butyl stearate, and propylene glycol; vitamins and derivatives thereof, such as panthenol and other derivatives of pantothenic acid, pantothenic ethers; vitamin penentration aids, such as polyethylene glycol or polypropylene glycol having from 3 to about 12 ethylene glycol or propylene glycol units, hair spray spray modifiers, such as polyethylene glycol having from about 2000 to about 25,000 ethylene glycol units. Such optional ingredients generally are used individually at levels from about 0:01% to about 10.0%, preferably from about 0.05% to about 5.0% of the composition.

METHOD OF USE

The hair care compositions of the present invention are used in conventional ways to provide the conditioning and damage protection benefits of the present invention. Such method of use depends upon the type of composition employed but generally involves application of a safe and effective amount of the product to the hair and allowed to remain on the hair. By "effective amount" is means an amount sufficient enough to provide a hair conditioning benefit. In general, from about 1 g to about 50 g is applied to the hair on the scalp. The composition is distributed throughout the hair by, typically by rubbing or massaging the hair and scalp with ones' hands, by another's hands or using a comb or brush. Preferably, the composition is applied to wet or damp hair prior to drying of the hair. After such compositions are applied to the hair, the hair is dried and styled in accordance with the desires of the user and in the usual ways of the user. Alternately, the composition is applied to dry hair, and the hair is then combed or styled in accordance with the desires of the user.

EXAMPLES

The following examples illustrate the present invention. It will be appreciated that other modifications of the present invention within the skill of those in the hair care formulation art can be undertaken without departing from the spirit and scope of this invention.

All parts, percentages, and ratios herein are by weight unless otherwise specified. Some components are obtained from suppliers as dilute solutions. The levels given reflect the weight percent of the active material, unless otherwise specified.

Hair Grooming Tonic

The following is a hair grooming tonic composition representative of the present invention.

| | Example No. | | | |
|---|---|---|---|---|
| Component (wt %) | 1 | 2 | 3 | 4 |
| Salcare ® SC96 (1) | 0.00 | 10.00 | 1.00 | 0.00 |
| Salcare ® SC95 (2) | 0.50 | 0.00 | 0.00 | 2.00 |
| Silicone Emulsion (3) | 0.00 | 1.00 | 2.00 | 0.50 |
| Perfume | 0.10 | 0.10 | 0.10 | 0.10 |
| Disodium EDTA | 0.15 | 1.50 | 0.15 | 0.15 |
| Ethanol | 0.00 | 98.05 | 70.00 | 0.00 |
| Water | 99.25 | 0.00 | 26.75 | 97.25 |

1. Polyquaternium 37 (and) Propylene Glycol Dicaprylate/Dicaprate (and) PPG-1 Trideceth 6, commercially available from Allied Colloids Ltd., (Norfolk, VA, USA).
2. Polyquaternium 37 (and) Mineral Oil (and) PPG-1 Trideceth 6, commercially available from Allied Colloids Ltd., (Norfolk, VA, USA).
3. Premix of polydimethylsiloxane gum/polydimethylsiloxane fluid (40:60 ratio) from GE Silicones and up to 30% polysorbate 80.

1. Polyquaternium 37 (and) Propylene Glycol Dicaprylate/Dicaprate (and) PPG-1 Trideceth 6, commercially available from Allied Colloids Ltd., (Norfolk, Va., USA).
2. Polyquaternium 37 (and) Mineral Oil (and) PPG-1 Trideceth 6, commercially available from Allied Colloids Ltd., (Norfolk, Va., USA).
3. Premix of polydimethylsiloxane gum/polydimethylsiloxane fluid (40:60 ratio) from GE Silicones and up to 30% polysorbate 80.

The composition is made by mixing the above components together in a conventional manner.

These compositions are found to have a viscosity, at 25° C., between 10 cP and 500 cP.

These compositions provide useful leave-on hair care products, which provide conditioning and damage protection benefits.

Non-aerosol Hair Sprays

Non-aerosol hair conditioning spray compositions of the present invention are prepared as follows:

| | Example No. | | | | |
|---|---|---|---|---|---|
| Component (wt %) | 5 | 6 | 7 | 8 | 9 |
| Salcare ® SC96 (1) | 1.00 | 0.00 | 0.70 | 2.00 | 1.00 |
| Salcare ® SC95 (2) | 0.00 | 1.00 | 0.00 | 0.00 | 0.00 |
| Silicone Emulsion (3) | 0.00 | 1.00 | 1.00 | 2.00 | 0.60 |
| PVP/VA Copolymer (4) | 0.00 | 1.00 | 0.00 | 2.00 | 1.00 |
| Polyethylene Glycol 4 | 0.50 | 0.50 | 0.00 | 0.50 | 0.45 |
| Polyethylene Glycol 5M | 0.005 | 0.01 | 0.00 | 0.10 | 0.01 |
| Disodium EDTA | 1.00 | 0.15 | 0.15 | 0.75 | 0.15 |
| Preservative | 0.35 | 0.35 | 0.35 | 0.35 | 0.35 |
| Fragrance | 1.00 | 1.00 | 1.00 | 1.00 | 0.05 |
| Ethanol | 0.00 | 70.00 | 0.00 | 0.00 | 0.00 |
| Panthenol | 0.05 | 0.02 | 0.00 | 0.02 | 0.05 |
| Crotein Q (5) | 0.00 | 0.00 | 0.02 | 0.00 | 0.01 |
| Panthenyl-Ethyl-Ether | 0.02 | 0.25 | 0.00 | 0.25 | 0.01 |
| OMC (6) | 0.00 | 0.00 | 0.00 | 0.00 | 0.01 |

-continued

| Component (wt %) | Example No. | | | | |
|---|---|---|---|---|---|
| | 5 | 6 | 7 | 8 | 9 |
| Silk Amino Acids (7) | 0.00 | 0.02 | 0.00 | 0.00 | 0.01 |
| Water | 97.00 | 24.99 | 96.80 | 91.90 | 96.30 |

1 Polyquaternium 37 (and) Propylene Glycol Dicaprylate/Dicaprate (and) PPG-1 Trideceth 6, commercially available from Allied Colloids Ltd., (Norfolk, VA, USA).
2 Polyquaternium 37 (and) Mineral Oil (and) PPG-1 Trideceth 6, commercially available from Allied Colloids Ltd., (Norfolk, VA, USA).
3 Premix of polydimethylsiloxane gum/polydimethylsiloxane fluid (40:60 ratio) from GE Silicones and up to 30% polysorbate 80.
4 PVP/VA (70/30) available from ISP
5 Hydrolyzed Animal Protein available from Croda, Inc.
6 Octylmethyoxy cinnamate, available from Givaudan-Roure, Inc.
7 Crosilk Liquid, available from Croda, Inc.

These products are prepared by dissolving the Salcare® $SC_{96}$ (1) in the water and/or ethanol and mixing for several minutes until all of the premix is dissolved. The remaining ingredients are then added. Fragrance is added last. All ingredients are added under mixing conditions. The product can be packaged in conventional nonaerosol pump spray containers and compressed air pump spray aerosol containers.

These compositions are found to have a viscosity, at 25° C., between 10 cP and 500 cP.

These compositions provide useful leave-on hair care products, which provide conditioning and damage protection benefits.

| Component (wt %) | Example No. | | |
|---|---|---|---|
| | 10 | 11 | 12 |
| Salcare ®SC96 (1) | 0.70 | 0.5 | 0.05 |
| Ethanol | 79.00 | 79.0 | 86.40 |
| Silicone Emuslion (2) | 0.50 | 0.00 | 1.00 |
| Diisobutyl Adipate | 0.70 | 0.00 | 0.00 |
| Potassium Hydroxide Solution (45% conc) | 1.00 | 1.00 | 1.00 |
| Gantrez ES225 ® (3) | 8.00 | 8.00 | 8.00 |
| Disodium EDTA | 0.15 | 0.15 | 0.15 |
| Perfume | 0.20 | 0.20 | 0.20 |
| Water | 9.75 | 11.15 | 3.20 |

1 Polyquaternium 37 (and) Propylene Glycol Dicaprylate/Dicaprate (and) PPG-1 Trideceth 6, commercially available from Allied Colloids Ltd., (Norfolk, VA, USA).
2. Premix of polydimethylsiloxane gum/polydimethylsiloxane fluid (40:60 ratio) from GE Silicones and up to 30% polysorbate 80.
3. Poly (methylvinyl ether/maleic acid) monoethyl ester, 50% solids in ethanol. Organic resin, commercially available from ISP.

These products are prepared by dissolving the Salcare® $SC_{96}$ in the ethanol and mixing for several minutes until all of the Salcare is dissolved. Diisobutyl Adipate is then added, if applicable. Potassium hydroxide is then added. Water and remaining ingredients are added. Fragrance is added last. All ingredients are added under mixing conditions. The product can be packaged in conventional nonaerosol pump spray containers and compressed air pump spray aerosol containers.

These compositions are found to have a viscosity, at 25° C., between 10 cP and 500 cP.

These compositions provide are useful as leave-on hair care products, which provide conditioning and damage protection benefits.

Mousse

The following is a hair mousse composition representative of the present invention.

| Premix Component (wt %) | Example No. | |
|---|---|---|
| | 13 | 14 |
| Salcare SC96 (1) | 0.54 | 2.15 |
| Silicone Emulsion (2) | 3.22 | 0.00 |
| Ethanol | 16.13 | 16.13 |
| Gaffix VC713 (3) | 4.30 | 5.38 |
| Cocamine oxide | 0.65 | 0.65 |
| Cocamide DEA | 0.32 | 0.32 |
| Polyethylene Glycol 4 | 0.48 | 0.38 |
| Panthenol | 0.05 | 0.16 |
| Perfume | 0.11 | 0.11 |
| Water | 74.20 | 74.73 |
| Total Premix Mousse | 100.00 | 100.00 |
| Premix | 93.00 | 93.00 |
| Isobutane Propellant | 7.00 | 7.00 |
| | 100.00 | 100.00 |

1 Polyquaternium 37 (and) Propylene Glycol Dicaprylate/Dicaprate (and) PPG-1 Trideceth 6, commercially available from Allied Colloids Ltd., (Norfolk, VA, USA).
2. Premix of polydimethylsiloxane gum/polydimethylsiloxane fluid (40:60 ratio) from GE Silicones and up to 30% polysorbate 80.
3 Vinyl caprolactam /PVP/ dimethylaminoethyl methacrylate copolymer. Organic resin, commercially available from ISP The compositions are made by blending all of the ingredients except isobutane at ambient temperature until well mixed. Aluminum aerosol cans are then filled with 93 parts of this batch, affixed with a valve which is crimped into position, and lastly pressure filled with 7 pads isobutane.

These compositions are found to have a viscosity, at 25° C., between 10 cP and 500 cP.

These compositions provide useful leave-on hair care products, which provide conditioning and damage protection benefits.

Example—Aerosol Hair Spray

An aerosol hair spray composition of the present invention is prepared as follows:

| Premix Component (wt %) | Example No. 15 |
|---|---|
| Salcare SC96 (1) | 1.27 |
| Silicone Emulsion (2) | 2.53 |
| Water | 3.80 |
| Polyethylene Glycol 4 | 0.48 |
| Panthenol | 0.15 |
| Ethanol | 80.18 |
| Gantrez ES225 (3) | 10.13 |
| Disodium EDTA | 0.19 |
| Potassium Hydroxide (45% solution) | 1.27 |
| Hair Spray Premix | 100.00 |
| Hair Spray Premix | 79.00 |
| Isobutane Propellant | 15.00 |
| Difluoroethane Propellant | 6.00 |
| | 100.00 |

1 Polyquaternium 37 (and) Propylene Glycol Dicaprylate/Dicaprate (and) PPG-1 Trideceth 6, commercially available from Allied Colloids Ltd., (Norfolk, VA, USA).
2 Premix of polydimethylsiloxane gum/polydimethylsiloxane fluid (40:60 ratio) from GE Silicones and up to 30% polysorbate 80.
3 Poly (methylvinyl ether/maleic acid) monoethyl ester, 50% solids in ethanol. Organic resin, commercially available from ISP.

All of the premix ingredients are mixed together at ambient temperature until the polymer is dissolved. The mixture is placed in an aerosol can which is then equipped with a conventional aerosol spray can valve which is vacuum crimped in place. The propellants are then filled through the valve and the can is equipped with a conventional aerosol spray can activator.

These compositions are found to have a viscosity, at 25° C., between 10 cP and 500 cP. These compositions provide are useful as leave-on hair care products, which provide conditioning and damage protection benefits.

What is claimed is:

1. A leave-on hair care composition comprising:
   (i) from about 0.1% to about 10%, by weight, of polyquaternium 37;
   (ii) from about 0.1% to about 10%, by weight, of disodium ethylene diamine tetra acetic acid;
   (iii) from about 60% to about 99.9%, by weight, of a polar solvent selected from the group comprising water, ethanol and mixtures thereof; and
   (iv) from about 0.1% to about 20%, of a hair care agent comprising a mixture of polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30;

wherein the weight ratio of said polyquaternium 37 to said disodium ethylene diamine tetra acetic acid is from about 1:1 to about 10:1; and wherein the viscosity of the composition is from about 10 cP to about 500 cP as measured using a Brookfield Viscometer, Spindle #41, at 25° C., at 10 RPM for three minutes.

2. A leave-on hair care composition comprising:
   (i) from about 0.1% to about 10%, by weight, of polyquaternium 37;
   (ii) from about 0.1% to about 10%, by weight, of disodium ethylene diamine tetra acetic acid;
   (iii) from about 60% to about 99.9%, by weight, of a polar solvent selected from the group comprising water, ethanol and mixtures thereof; and
   (iv) from about 0.1% to about 20%, of a hair care agent comprising a copolymer of polyvinyl pyrrolidone and vinyl acetate;

wherein the weight ratio if said polyquaternium 37 to said disodium ethylene diamine tetra acetic acid is from about 1:1 to about 10:1; and wherein the viscosity of the composition is from about 10 cP to about 500 cP as measured using a Brookfield Viscometer, Spindle #41, at 25° C., at 10 RPM for three minutes.

3. A leave-on hair care composition comprising:
   (i) from about 0.1% to about 10%, by weight, of polyquaternium 37;
   (ii) from about 0.1% to about 10%, by weight, of disodium ethylene diamine tetra acetic acid;
   (iii) from about 60% to about 99.9%, by weight, of a polar solvent selected from the group comprising water, ethanol and mixtures thereof; and
   (iv) from about 0.1% to about 20%, of a hair care agent comprising a mixture of polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, and a copolymer of polyvinyl pyrrolidone and vinyl acetate;

wherein the weight ratio of said polyquaternium 37 to said disodium ethylene diamine tetra acetic acid is from about 1:1 to about 10:1; and wherein the viscosity of the composition is from about 10 cP to about 500 cP as measured using a Brookfield Viscometer, Spindle #41, at 25° C., at 10 RPM for three minutes.

4. A method for conditioning human hair comprising the application of a safe and effective amount of the hair care composition according to claim 3 to the hair of a human in need of such treatment.

* * * * *

UNITED STATES PATENT AND TRADEMARK OFFICE
CERTIFICATE OF CORRECTION

PATENT NO. : 5,674,478

DATED : October 7, 1997

INVENTOR(S) : Michael Thomas Dodd et al.

It is certified that error appears in the above-identified patent and that said Letters Patent is hereby corrected as shown below:

On the title page, item [22], "January 16, 1996" should read --January 12, 1996--.

At column 3, line 3 "#-41" should read --#41--.

At column 5, line 28 "$SC_{95}$" should read --SC95--.

At column 5, line 32 "$SC_{96}$" should read --SC96--.

At column 5, line 41 "salt Of the" should read --salt of the--.

At column 6, line 62 "solvents am" should read --solvents are--.

At column 9, line 11 "100,0.00 centistokes" should read --100,000 centistokes--.

At column 10, line 38 "PVPNA" should read --PVP/VA--.

At column 11, line 2 "Apr. 14 1992 U.S." should read --Apr. 14, 1992, U.S.--.

At column 11, line 3 "07/758,319 Bolich" should read --07/758,319, Bolich--.

At column 11, line 4 "07/758,320 Torgerson" should read --07/758,320, Torgerson--.

At column 11, line 39 "0:01%" should read --0.01%--.

UNITED STATES PATENT AND TRADEMARK OFFICE
CERTIFICATE OF CORRECTION

PATENT NO. : 5,674,478
DATED : October 7, 1997
INVENTOR(S) : Michael Thomas Dodd et al.

It is certified that error appears in the above-identified patent and that said Letters Patent is hereby corrected as shown below:

At column 13, line 19 "$SC_{96}$" should read --SC96--.

At column 13, line 51 "$SC_{96}$" should read --SC96--.

At column 14, line 31 "7 pads" should read --7 parts --.

At column 16, line 1 "0. i%" should read --0.1%--.

At column 16, line 4 "ratio if said" should read --ratio of said--.

At column 16, line 6 "1;1" should read --1:1--.

Signed and Sealed this

First Day of June, 1999

Q. TODD DICKINSON

Attest:

Attesting Officer

Acting Commissioner of Patents and Trademarks